(12) United States Patent
Bernini et al.

(10) Patent No.: US 10,691,308 B2
(45) Date of Patent: Jun. 23, 2020

(54) CONTROLLING THE DISPLAY OF A DATASET

(75) Inventors: Nicole Bernini, Burgdorf (CH); Christoph Rickert, Reinach (CH); Andrea Schuetz Frikart, Ostermundigen (CH); Reto Sigrist, Golaten (CH); Beat Spoerri, Bibern (CH)

(73) Assignee: Roche Diabetes Care, Inc., Indianapolis, IN (US)

( * ) Notice: Subject to any disclaimer, the term of this patent is extended or adjusted under 35 U.S.C. 154(b) by 325 days.

(21) Appl. No.: 13/560,469

(22) Filed: Jul. 27, 2012

(65) Prior Publication Data

US 2013/0198685 A1  Aug. 1, 2013

(30) Foreign Application Priority Data

Jul. 28, 2011 (EP) ................................. 11006203

(51) Int. Cl.
*G06F 3/0484* (2013.01)
*G16H 40/63* (2018.01)
*G06F 3/01* (2006.01)

(52) U.S. Cl.
CPC ........... *G06F 3/0484* (2013.01); *G16H 40/63* (2018.01); *G06F 3/01* (2013.01)

(58) Field of Classification Search
CPC . A61M 2205/502–507; A61M 2205/583–585; A61M 2230/201;
(Continued)

(56) References Cited

U.S. PATENT DOCUMENTS 5,452,416 A * 9/1995 Hilton .................. G06F 19/321
345/424
5,772,635 A * 6/1998 Dastur .................. A61M 5/172
604/131

(Continued)

FOREIGN PATENT DOCUMENTS

EP 0 830 170 B1 3/2004
EP 1986152 A2 10/2008
(Continued)

OTHER PUBLICATIONS

Merriam-Webster.com entry for "abbreviate", published at https://www.merriam-webster.com/dictionary/abbreviate and dated Feb. 21, 2010 per Internet archive Wayback Machine capture.*
(Continued)

*Primary Examiner* — Daniel Samwel
(74) *Attorney, Agent, or Firm* — Bose McKinney & Evans LLP

(57) ABSTRACT

A medical system comprising a display is presented. In response to the reception of triggering information, a subset of data is selected from a displayed or non-displayed dataset according to a data priority scheme and the displayed dataset is replaced by the display of the selected subset of data. The display of the selected subset of data uses a variety of rendering options. The triggering information is provided by the user or provided by one or more sensors. The data priority scheme is predefined or computed. It is static or dynamic. The data priority scheme can comprise a threshold which is applied for the selection or determination of the subset of data. Examples of priorities associated with data for diabetes care are provided. A range of displays can be used and combined.

15 Claims, 10 Drawing Sheets

(58) Field of Classification Search
CPC ............. G06F 19/3406; G06F 19/3468; G06F 2203/04806; G06F 3/0484; G06F 3/01; G16H 40/63
USPC .................................................. 715/700–866
See application file for complete search history.

(56) References Cited

U.S. PATENT DOCUMENTS

| | | | | |
|---|---|---|---|---|
| 6,554,798 | B1* | 4/2003 | Mann | A61M 5/14244 604/131 |
| 2001/0025189 | A1* | 9/2001 | Haueter | G06F 19/00 607/62 |
| 2003/0159113 | A1* | 8/2003 | Bederson | G06F 17/27 715/252 |
| 2004/0015102 | A1* | 1/2004 | Cummings | A61B 5/7475 600/584 |
| 2005/0192557 | A1* | 9/2005 | Brauker | A61B 5/0002 604/503 |
| 2005/0229110 | A1* | 10/2005 | Gegner | G06F 3/0481 715/800 |
| 2006/0082542 | A1 | 4/2006 | Morita et al. | |
| 2007/0083193 | A1* | 4/2007 | Werneth | A61B 5/0422 606/41 |
| 2007/0124501 | A1* | 5/2007 | Lee | G06F 17/214 709/246 |
| 2008/0113688 | A1 | 5/2008 | Lee et al. | |
| 2008/0144107 | A1 | 7/2008 | Lieb | |
| 2008/0255438 | A1* | 10/2008 | Saidara | A61B 5/14532 600/365 |
| 2008/0300572 | A1* | 12/2008 | Rankers | A61B 5/14532 604/504 |
| 2009/0069787 | A1 | 3/2009 | Estes et al. | |
| 2009/0100364 | A1* | 4/2009 | Kinoshita | A61B 5/00 715/765 |
| 2009/0113295 | A1* | 4/2009 | Halpern | A61B 5/14532 715/273 |
| 2009/0147026 | A1* | 6/2009 | Buck | G06F 3/0481 345/666 |
| 2009/0213078 | A1* | 8/2009 | Christopher | G06F 3/04895 345/169 |
| 2009/0240120 | A1* | 9/2009 | Messinger | A61B 5/7445 600/301 |
| 2009/0275886 | A1* | 11/2009 | Blomquist | G09G 3/344 604/66 |
| 2009/0326445 | A1* | 12/2009 | Graskov | A61M 5/1723 604/67 |
| 2010/0004598 | A1* | 1/2010 | Eberhart | A61M 5/14244 604/151 |
| 2010/0131482 | A1 | 5/2010 | Linthicum et al. | |
| 2010/0131883 | A1 | 5/2010 | Linthicum et al. | |
| 2010/0167385 | A1 | 7/2010 | Celentano et al. | |
| 2010/0188426 | A1* | 7/2010 | Ohmori | G06F 3/012 345/660 |
| 2011/0001605 | A1* | 1/2011 | Kiani | G06F 19/327 340/5.6 |
| 2011/0130716 | A1* | 6/2011 | Estes | A61M 5/1413 604/66 |
| 2011/0152657 | A1* | 6/2011 | Bielawa | G01N 33/48792 600/365 |
| 2011/0193704 | A1* | 8/2011 | Harper | A61B 5/14532 340/573.1 |
| 2011/0202490 | A1* | 8/2011 | Gawlick | G06F 19/00 706/47 |
| 2011/0313349 | A1* | 12/2011 | Krulevitch | A61M 5/24 604/65 |
| 2012/0165620 | A1* | 6/2012 | Tanis | A61N 7/00 600/301 |
| 2012/0319848 | A1* | 12/2012 | Coffeng | 340/573.1 |
| 2013/0245545 | A1* | 9/2013 | Arnold | A61M 5/1723 604/66 |

FOREIGN PATENT DOCUMENTS

| | | |
|---|---|---|
| EP | 2284675 A2 | 2/2011 |
| WO | WO 2009/135108 A2 | 11/2009 |
| WO | WO 2011/026053 A1 | 3/2011 |
| WO | WO 2011/056839 A1 | 5/2011 |

OTHER PUBLICATIONS

Merriam-Webster.com entry for "magnify", published at https://www.merriam-webster.com/dictionary/magnify and dated Feb. 19, 2010 per Internet archive Wayback Machine capture.*

* cited by examiner (a)

(b)

(c)

(d)

| Data entry | Priority rank | Auto-matic | User defined | ... | Icon |
|---|---|---|---|---|---|
| Bolus dose | 1 | Y | Y | ... | ... |
| Basal rate | 1 | N | Y | ... | 🏙 |
| ... | ... | ... | ... | ... | ... |
| Date and time | 4 | N | 4 | ... | ... |

| | Priority rank | | | | |
|---|---|---|---|---|---|
| Information | Day | Night | Work | ... | Lunch |
| Basal | 1 | 1 | 3 | ... | 3 |
| Basal Temporary Rate | 1 | 1 | 4 | ... | 3 |
| Bolus Multiwave | 1 | 4 | 4 | ... | 2 |
| Bolus Standard | 1 | 4 | 4 | ... | 1 |
| Cartridge | 2 | 2 | 4 | ... | 4 |
| Lag | 2 | 4 | 4 | ... | 2 |
| Leakage | 2 | 4 | 4 | ... | 4 |
| Maintenance | 2 | 2 | 4 | ... | 4 |
| Mode (flight, ...) | 4 | 4 | 4 | ... | 4 |
| Occlusion | 1 | 1 | 1 | ... | 1 |
| Pairing | 4 | 4 | 4 | ... | 4 |
| Pump memory | 3 | 4 | 4 | ... | 4 |
| Pump timer | 3 | 4 | 4 | ... | 4 |
| Quick Bolus | 1 | 4 | 4 | ... | 1 |
| Time | 2 | 4 | 4 | ... | 4 |
| Warning | 1 | 1 | 1 | ... | 3 |

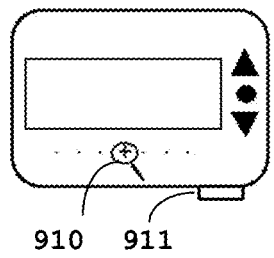 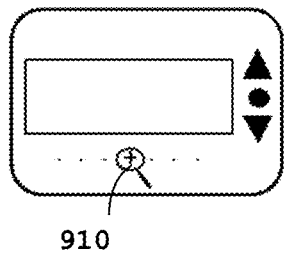 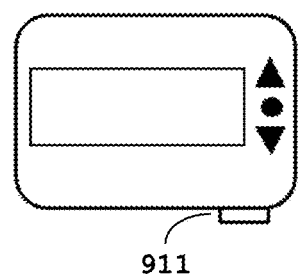
Fig.9a    Fig.9b    Fig.9c
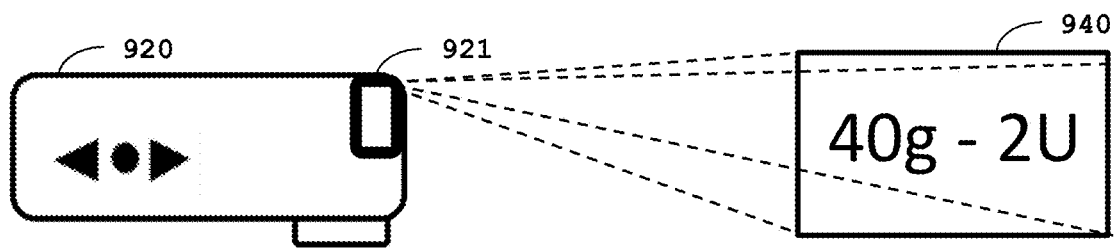
Fig.9d
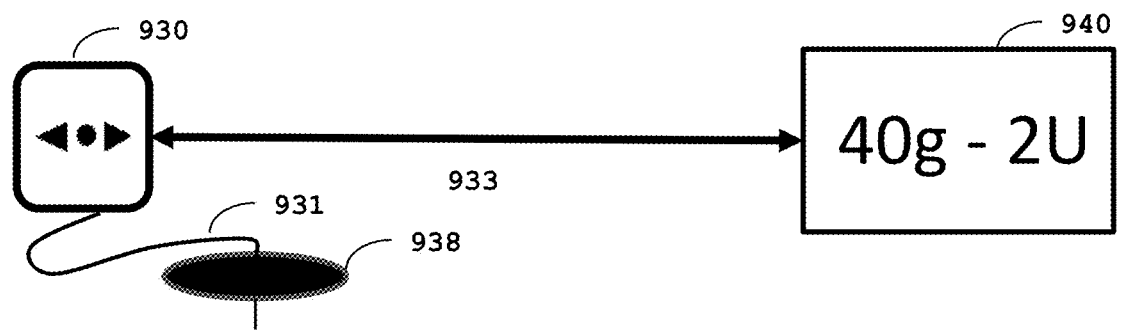
Fig.9e

CONTROLLING THE DISPLAY OF A DATASET

CROSS-REFERENCE TO RELATED APPLICATIONS

This application is based on and claims priority to EP 11006203.1, filed Jul. 28, 2011, which is hereby incorporated by reference.

BACKGROUND

The present disclosure generally relates to controlling the display of a dataset and, in particular, to the methods and systems of selecting, adapting or optimizing the display of a selected subset of a dataset.

There is a need for improvements of current methods and systems for controlling a display device of an electronic device for enhanced readability, in particular for visually impaired persons.

SUMMARY

According to the present disclosure, a medical system is presented. The medical system comprises a display. In response to the reception of triggering information, a subset of data is selected from a displayed dataset according to a data priority scheme and the displayed dataset is replaced by the display of the selected subset of data.

Accordingly, it is a feature of the embodiments of the present disclosure to provide improvements of current methods and systems for controlling a display device of an electronic device for enhanced readability, in particular for visually impaired persons. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 9 illustrates examples of different embodiments and architectural choices, with different triggering information interfaces and/or different display devices and/or different communication modes according to an embodiment of the present disclosure.

DETAILED DESCRIPTION

Figure 1:
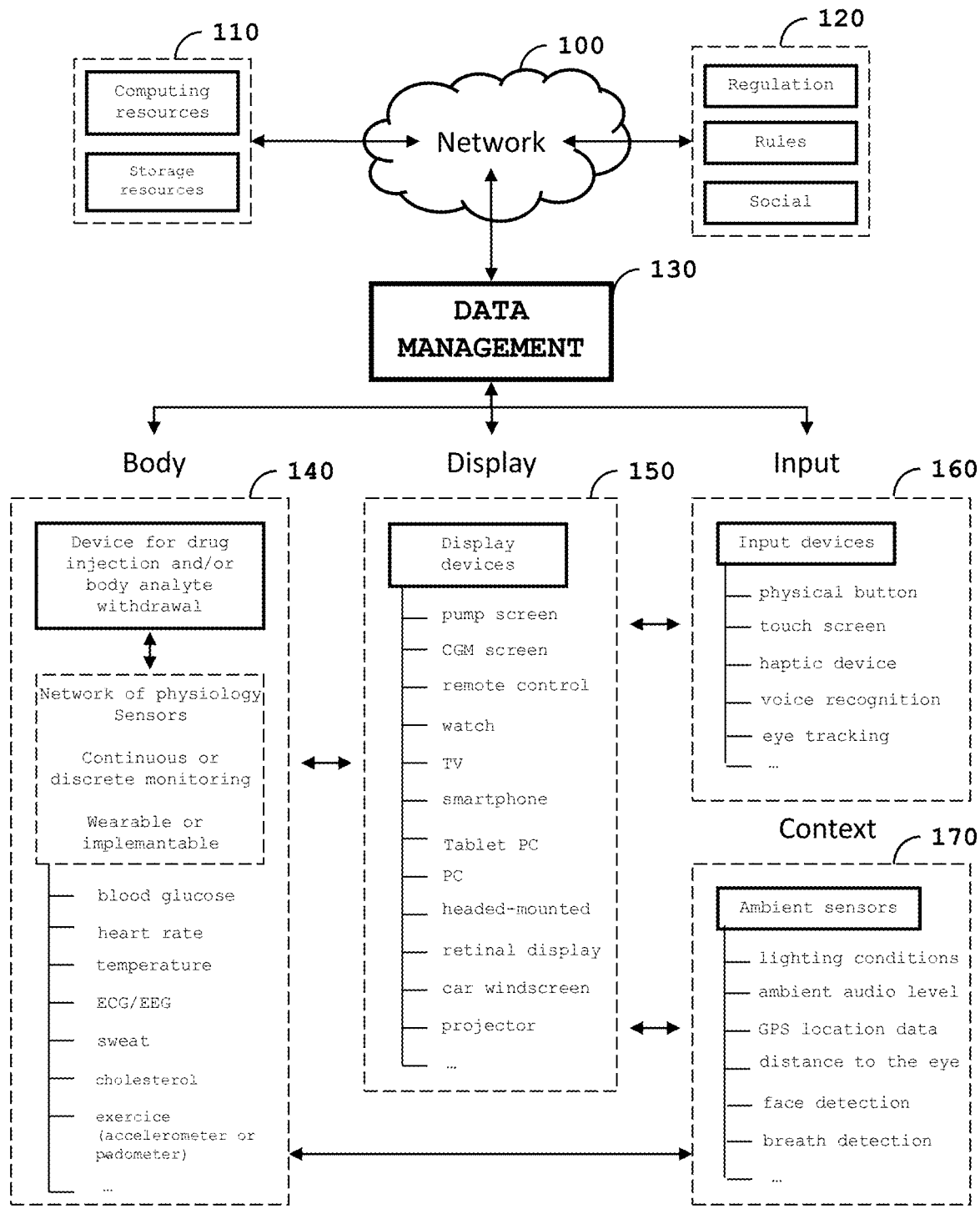
FIG. 1 illustrates system view and architectural choices according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The present disclosure discloses methods and systems of selecting a subset of data of a dataset, automatically or on demand, and of adapting or optimizing the display of the selected subset of data according to certain data priority schemes. There are provided contextual and/or proactive display methods and systems. The medical product related to the present patent application is one of the first insulin pump brought to the market provided with zoom functionality, corresponding to one embodiment of disclosed methods and systems.

Examples are provided to adapt the display of data to specific contexts. Regarding the form, a modified display can occur either on demand or automatically. The display of data can be managed according to certain technical parameters, predefined or not, static or dynamic, optionally retrieved in real-time. Optional sensors (and the combinations thereof) can lead to appropriate displays of particular data. Regarding the substance, a selection process of a subset of data is described. Form and substance being intermingled, the methods and systems presently described do accordingly combine the appropriate use of triggering information, the appropriate selection processes or definition of data priority schemes and the appropriate presentation of information determined and enabled by technical methods.

Effects or advantages or objectives can relate to enhanced readability, better downstream human decisions, gain of time due to faster access to contextually relevant information, increased ease of use due to increased relevancy of the displayed data, increased comfort, contextual provision of data, better security, increased medical safety, etc. The absolute relevancy or contextual/relative relevancy can be being appreciated with respect to the environment of the user (noisy or quiet, dark or light, etc.) or with respect to the context (activities) in which the user is (night or day, work, lunch time, calendar day and habits) or even with respect to the state of the user (sleeping, just awakening, working, relaxing, etc.) for example.

The disclosed methods and systems can be a benefit in particular to visually impaired persons, but not only those persons. Embodiments of the present invention can also be a benefit to several types of persons or audiences: Sick persons such as, for example, anemic patients who track their blood oxygen levels and want to be notified about contextually relevant information. Likewise, cardiac persons can be alerted in case of increased probability of faintness. Persons with chronic diseases, and diabetes in particular; some diabetics are visually impaired, since over the years the chronic disease may have caused harm to their eyes and in particular to their retinas. Persons with diabetes having normal vision capabilities can also benefit from the present disclosure. In everyday life, a better user interaction with the insulin pump or other components of an insulin delivery system (for example, a remote control device such as a blood glucose meter having remote control capabilities for controlling the operation of the pump) can provide more comfort. The vision capabilities of these persons being diminished, a particular handling of the management of the display of the data is required. The elderly in developed countries, the aging of the population, can be associated with more frequent vision problems.

The agility with user interfaces can also diminish. Therefore, more simple and effective user interfaces are needed. The present methods and systems can enable the provision of effective user interfaces. Children, in some situations, users or patients may be very young. Adapted display methods and systems, particular user interaction can be required. Sustained attention capabilities and educational levels may lead to a particular style of communication, for example with icons and/or with images and/or with videos and/or with figures and/or with a combination thereof. Healthy individuals, these persons can also have an interest in the disclosed methods and systems for preventive medicine or fitness monitoring purposes for example. For example, a person participating in sports, such as a cyclist, may closely monitor his sodium levels to prevent dehydration. A jogger may monitor his heart rate and be notified of relevant information. While participating in sport, there can be little time for looking at the display of data on display devices. Audio signals such as text to speech lectures of heart rate for example may not be convenient enough in noisy environments. A visual display can remain useful but the display may have to be optimized regarding a set of parameters (user profile, date and time, data characteristics, display characteristics, etc.). Preventive or personalized medicine may implement present methods and systems. For example, a person presenting risks regarding cholesterol levels may be interested in appropriate prompts of measured levels (continuous monitoring basis or intermittent basis), in order to modify his behavior at certain particular moments in life (lunches). Soldiers or police or military forces, on the battlefield, the continuous monitoring of toxic agents and the associated optimized display of information may result in increased survival chances. Applications can correspond to the remote sensing of airborne bacteria e.g., in counter-bioterrorist activities (detection of pathogens) or to the determination or handlings of levels of toxic substances before and after bioremediation.

Optimized displays can thus intervene at special moments, particular moments, episodic moments, regular moments or even random moments (form). The presentation of information can be optimized according to a technical logic and by technical methods. Contents can be optimized (substance).

Referring initially to FIG. 1, a system view and architectural choices for implementing disclosed methods in/or systems is illustrated. FIG. 1 comprises a network 100, computing and storage resources 110, regulation, rules and social rules or features 120, data management processes and associated logic 130, a set of body sensors 140, displays 150, inputs devices or interfaces 160, and contextual or ambient sensors 170. The network 100 may be any network, such as, for example, Internet, Intranet, Wi-Fi, or a mesh network (ad-hoc network). It can correspond, in particular, to the network enabling a system of networked medical devices.

Computing resources and storage resources 110 can be associated with processors and storage or memory units. These resources 110 can be local (physical implementation of the resources in the drug infusion device for example) or remotely accessed (through the network, in the "cloud" for example). An insulin pump can comprise a processor and a memory unit, for example. In the future, insulin pumps may correspond to a thin client controlled in/by the cloud.

The rules 120 may comprise regulation rules provided by regulatory authorities. Such rules may be provided in the form of pieces of software code provided through the network (firmware and/or software and/or hardware embodiments). Other rules can be shared by communities of patients (leveraging social features and sharing of experiences through the network). For example, such a rule might read "if it is 11 am and the blood glucose measurement is below 70, then verify the continuous monitoring sensor". Such rules may be updated with firmware updates of the pump (or of any networked medical devices of the medical system, sharing such rules within the system). Other embodiments can correspond to hardware embodiments (i.e. storage in ROM or USB sticks, for example).

The data management processes or logic 130 can operate or occur in the cloud or locally, such as in a medical infusion pump. It can comprise a priority scheme. The data priority scheme can comprise a knowledge base of facts, a set of rules, priority ranks, or other components. The priority scheme can be static (i.e. the components do not evolve over time) but it may also be dynamic (priority ranks evolve over time, and/or are responsive to local events and/or regulation rules and/or user profiles or preferences and/or contextual data and/or environmental data and/or ambient data). The priority scheme will be described in detail in FIG. 8.

Body sensors 140 can form a Body Area Network (BAN) or Body Sensor Network (BSN). Body sensors 140 can comprise wearable and/or implementable and/or wireless (bio) sensors to assess the physiological state of the user or patient. These sensors 140 can monitor the physiological state continuously or not (on demand or upon action of the user). For example, the following parameters can be monitored: blood glucose, heart rate, body temperature, ECG, EEG, EMG, sweat, blood cholesterol, blood alcohol, coagulation, and estimation of physical exercise or carbs consumption (such as evaluated by accelerometers or pedometers for example).

Body sensors 140 can comprise, for example:
1) Accelerometer/gyroscope: an accelerometer can be used to recognize and monitor body posture, such as sitting, kneeling, crawling, laying, standing, walking and running. Such ability can be essential to many applications, including virtual reality, healthcare, sports and electronic games. The accelerometer-based posture monitoring for BANs typically consists of 3-axis accelerometers (or tri-axial accelerometers) which can be placed on some strategic locations on a human body. They can also be used to measure the vibration, as well as acceleration due to the gravity. A gyroscope can be used for measuring or maintaining orientation, based on the principle of conservation of angular momentum.

Gyroscopes can be used together with accelerometers for physical movement monitoring;

2) Blood glucose (BG): also called blood sugar, can be the amount of glucose circulating in the blood. Traditionally, glucose measurements are done by lancing a finger and extracting a drop of blood, which is applied to a test strip that includes chemicals sensitive to the glucose in the blood sample. An optical or electrochemical detector (glucometer) can be used to analyze the blood sample and can give a numerical glucose reading. Recently, non-invasive glucose measuring devices that monitor BG through infrared technology and optical sensing have become available;

3) Blood pressure: the blood pressure sensor can be a non-invasive sensor designed to measure systolic and diastolic human blood pressure utilizing the oscillometric technique;

4) $CO_2$ gas sensor: the $CO_2$ gas sensor measures gaseous carbon dioxide levels to monitor changes in $CO_2$ levels as well as to monitor oxygen concentration during human respiration;

5) ECG sensor: ECG is a graphic record of the heart's electrical activity. Healthcare providers use it to help diagnose a heart disease as well as to monitor how well different heart medications are working. In order to obtain an ECG signal, several electrodes can be attached at specific sites on the skin (e.g., arms, and chest) and the potential differences between these electrodes are measured;

6) EEG sensor: the EEG sensor measures the electrical activity within the brain by attaching small electrodes to the human's scalp at multiple locations. Then, information of the brain's electrical activities sensed by the electrodes can be forwarded to an amplifier for producing a pattern of tracings. Synchronous electrical activities in different brain regions are generally assumed to imply functional relationships between these regions. In a hospital, the patient may be asked to breathe deeply or to look at a flashing light during the recording of EEG;

7) EMG sensor: the EMG sensor measures electrical signals produced by muscles during contractions or at rest. Nerve conduction studies are often done together with measuring the electrical activity in muscles, since nerves control the muscles in the body by electrical signals (impulses) and these impulses make the muscles react in specific ways. Nerve and muscle disorders cause the muscles to react in abnormal ways;

8) Pulse Oximetry: pulse oximetry measures oxygen saturation using a non-invasive probe. A small clip with a sensor is attached to the person's finger, earlobe, or toe. The sensor gives off a light signal that passes through the skin. According to the light absorption of oxygenated hemoglobin and total hemoglobin in arterial blood, the measurement is expressed as a ratio of oxygenated hemoglobin to the total amount of hemoglobin;

9) Humidity and temperature sensors: these sensors are used for measuring the temperature of the human body and/or the humidity of the immediate environment around a person. An alarm signal can be issued if a certain amount of changes are measured; and 10) Image of video sensors: by computer vision, data can be extracted or inferred from data streams.

The data or signals provided by these sensors can be integrated by a central logic (not shown), which can define a global assessment of the state of the patient: sleeping, just awakened, having lunch, tired, relaxed, busy, energized, euphoric, drunk, etc. External or exogenous parameters such as calendar data and/or time data can be efficiently combined and used in order to increase the probability of accuracy of the assessment. Real examples and situations will be provided in FIG. 2.

The display 150 can be for example a screen of an insulin pump, a screen of a continuous glucose monitoring CGM-based device, a screen of a remote controller, a screen on a watch, a television, a screen of the smart phone, a tablet PC, a PC screen, a headed-mounted display, a retinal projector display, a display projected on a car windscreen (augmented reality), a traditional projector, a projector beaming an image on a wall or on any other surface with appropriate geometrical corrections in response to the deformations of the projecting surface, etc. It is important to note that a combination of screens or displays can be used simultaneously. In other words, data displayed to the user can be distributed across several different devices. A blood glucose value can be displayed on a screen at immediate proximity of the patient while information of secondary importance can be displayed on other devices according to an opportunistic approach. Such an example will be described in more detail in FIG. 10.

Inputs devices 160 can comprise devices such as one or more physical buttons, a touchscreen or a portion thereof, a voice recognition device, eye-tracking device, etc. A wide range of haptic devices can also be used and such devices also include motion gestures analysis or interpretation. The devices can be combined with one another (multimodal interaction). For example, a voice command can be confirmed or modulated by an action on a touch sensitive interface.

Contextual sensors 170 can be sensors which can be present in the environment (RFID tags providing GPS information, nutritional values of meals, etc.) or worn by the patient. Some may also be implemented in the body of the user. These sensors can assess the current lighting conditions (night, dark, sunny, etc.), can probabilistically assess or classify the ambient audio level (restaurant, nightclub, working environment, sleeping room, outdoor activities assessed by the presence of wind sounds for example, indoor activities assessed by the presence of particular acoustic responses or audio signals such as music for example), can determine a geographical location such as a GPS sensor for example, can perform human face detection (the device can continuously monitor this parameter in order to provide an appropriate response upon the detection of the face of the user looking at the medical infusion device for example), can evaluate the distance to the eye of the user—a user looking at the insulin pump screen will need different enlargements if standing at 1 m (during the day) compared to 10 centimeters (during the night) for example, can detect the breath of the user (when the user stands very close to the device, for example, during the night). The sensors mentioned above can be combined. For example, the proximity of the user face can be confirmed by the detection of the breath of the user in the proximity of the sensor.

The sensors described above (contextual and body sensors) can be combined together. For example, a blood glucose sensor can integrate with a sensor that can assess the current lighting conditions and can lead to the display of some particular data, in a particular manner. Some or all of the above architectural elements can be in interaction with each other. For example, the data management processes or logic can be influenced by ambient sensors but also by rules 120 input by a user or a healthcare provider, or even retrieved from the network 100. For example, such rules 120 can be open source rules provided by communities of users or patients. In one embodiment, the disclosed method and system can take the form of a local medical system totally independent from a network and may comprise a drug delivery system, such as a patch pump attached to the skin of a user or patient, a remote controller of the delivery system (for example, having the display, shape and design of a smart phone). According to such an embodiment, computing and storage resources can be local, i.e. physically present in the delivery system and/or in the remote controller. In this view, the display may most likely to be present on the remote controller, since the delivery device is desired to be as small as possible (yet a flexible screen may be incorporated on a micro-pump for example). These can be mainly autonomous systems.

According to another embodiment, computing and storage resources can be located in the cloud (in one or more servers accessible by one or more communication channels to a medical system). The local device, namely an infusion device, can comprise the core medical features (drug reservoir, source of energy, motor or equivalent, injection and/or withdrawal devices for continuous or intermittent monitoring for example). It may further comprise communication capabilities (according to continuous or episodic or intermittent or even opportunistic modes). In other words, a computer (processor) and storage (memory unit) can be remotely accessed. According to this view, the display embodiment can remain mostly unchanged. The rendering of the data to be displayed may be handled in the cloud. The local display device can then act as a display device (i.e. the images being communicated to the local display device can be uncompressed and do not need local processing steps). Of course, as discussed, numerous intermediate embodiments or variants are possible. For example, some processing capabilities (image processing such as uncompressing capabilities for example) may be present at the local level.

The embodiments discussed above where computing and storage resources are local or found in the cloud are two examples. Many intermediate embodiments with a different allocation of computing and storage resources between a (networked) device and the cloud are possible. For example, in some embodiments, computing and storage resources used to monitor and safely operate a medical device might be local, whereas computing and storage resources of the cloud can be utilized for analyzing medical data to provide a user with tools for improving their lives. In another example, a set of networked medical devices can be used. A glucometer with the look and feel of a mobile phone (or a mobile phone having a hardware extension providing glucose measurement capabilities) can act as the central device. It can command a pump (a micro-pump or patch-pump attached to the skin of the user, or a pump worn on a belt by the patient, or as a pager, etc.), which can communicate with a continuous monitoring device. The two devices (pump and continuous monitoring devices) can be integrated into one. A web platform can retrieve the data collected by one or more considered devices, in order to perform correlation operations (data of one individual can be compared to other data of other patients or to historical data, for statistical purposes, etc.). A patient can upload his personal data on demand, or the process can happen automatically (in continuous, on-the-fly or intermittently). A computer accessing the platform may display certain type of information or enable the user to setup the data priority scheme and to share it on social networks.

Data (personal data, profile data, displayed data, rules, facts, etc) can be distributed over the local networked devices and/or in the cloud. The data priority scheme can be downloaded from the cloud, and/or can be merged with a local data priority scheme, and/or can be locally defined, and/or can be dynamically defined. Each networked device may have its own data priority scheme. Alternatively, networked devices may share a common data priority scheme, centralized or distributed. Rules, priority tasks or data can be present in firmware or in software or in hardware or in a combination thereof. Even processing resources or storage resources can be so distributed. Distributed computing can enable networked devices to cooperate. If the CPU capabilities of the pump are saturated, it can be possible to use processing capabilities of the remote controller for example. Processing tasks can be shared between devices or switched from a device to another. Likewise, storage also can be distributed. A networked USB key of the patient can serve as a hard drive for the pump, or as a key for decryption of data, etc.

The same remarks can apply for the display devices. One main screen or display may handle the display of all or part of the data, but several displays may handle in cooperation the "global" display (i.e. the interaction towards the user). The glucometer may display some type of information (such as blood glucose and basal information), while the pump could "specialize" in maintenance information. The CGM based device (continuous monitoring device) could display blood glucose and probabilistic expected evolution of the glucose level. The present method can be of advantage for the CGM device. When the blood glucose is decreasing too rapidly, this can act as the "triggering information." When the CGM magnifies the current measurement, it can send a command for magnification (or any other rendering effect) to the central display implemented on the pump and/or on the remote controller and/or glucometer. Prompts can be remotely commanded (parents of a child with the chronic disease may be prompted by an active window appearing on their desktop because of a triggering information such as a fast decrease in blood glucose).

Online and offline modes of the medical system (and/or of each one of the medical devices part of said system) can be possible. The networked devices may indeed operate according to online and/or offline modes. Data caching may enable the devices to be autonomous.

Figure 2:
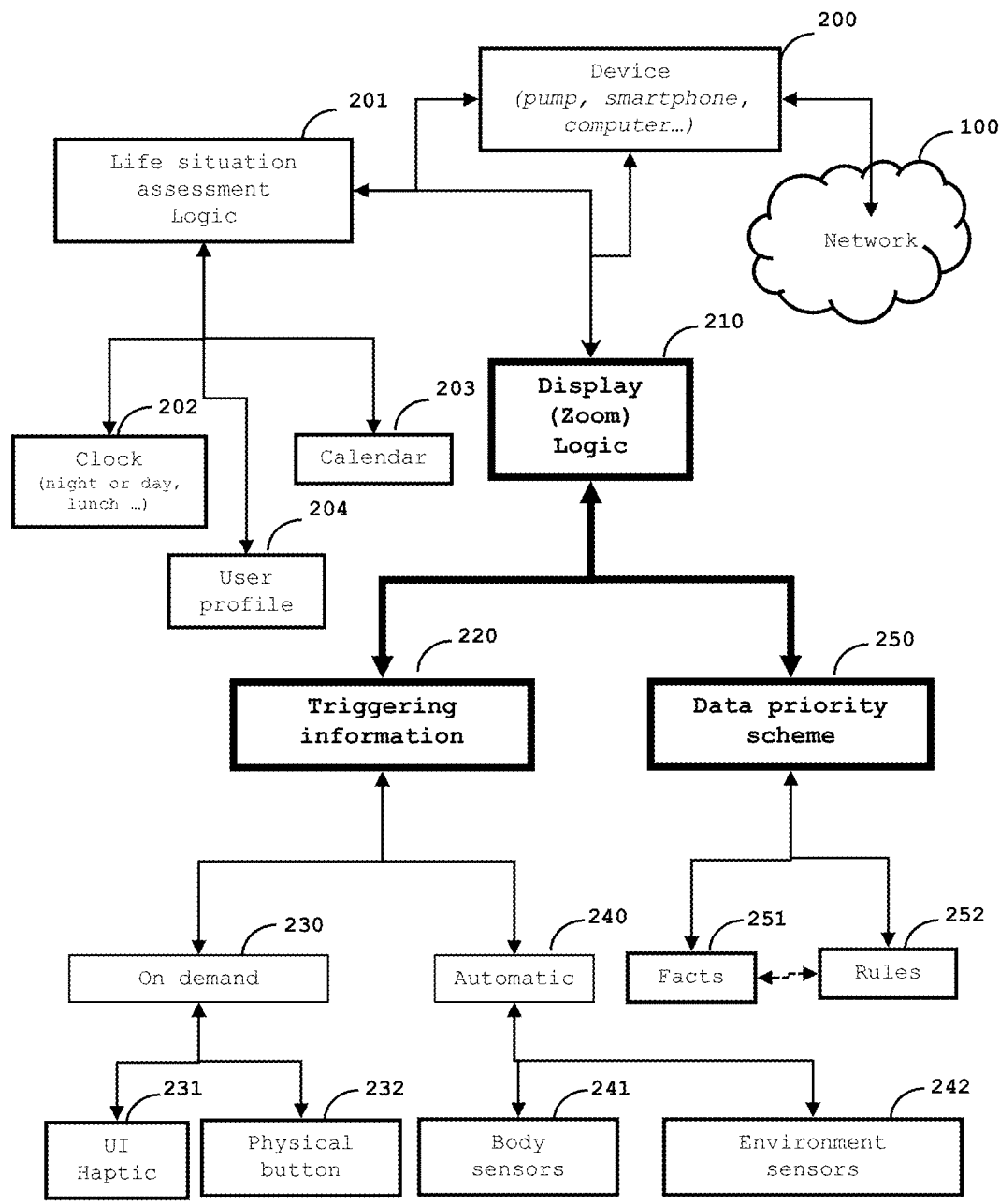
FIG. 2 illustrates overview and workflow of the method according to an embodiment of the present disclosure.

The FIG. 2 shows an overview and workflow in an embodiment of the disclosed method that can be implemented. FIG. 2 can comprise a network 100, one or more devices 200 (for example, one or more of a medical infusion pump, a remote control device such as a blood glucose meter functioning as a remote control, a continuous blood glucose monitor, a smart phone functioning as a remote control, or a computer for programming the medical infusion pump), a life situation assessment logic 201 accessing data of a clock 202 (night or day, lunchtime, etc), a calendar 203, the user profile 204, a display logic 210, a data priority scheme or model 250, and a Triggering Information device or system or surface or command 220.

A display logic 210 can control the display of the devices 200. It can integrate the data provided by the life situation assessment logic 201, optionally with data associated with the triggering information 220 and/or with the data priority scheme 250.

Regarding the nature and possible embodiments of the triggering information unit 220, it can be possible to distinguish two main modes:

a) "on demand" mode: According to this embodiment, a zoom function can be triggered by user actions on a physical button for example. Alternatively, the user can shake the device. The accelerometer can then interpret this motion as the need or request for displaying the most important data, namely current blood glucose level and/or basal rate. The user also can trigger such a display by a particular action on the touchscreen. Alternatively, voice or sound commands captured by a microphone can trigger such data display.

b) "automatic" mode: Instead a triggering information coming explicitly from the user (reactive mode), an automatic mode (proactive mode) may present many advantages. Among other benefits, the comfort of use can be increased. The efficiency of the interaction of the user with the device can be increased. The system can permanently adapt to the user activities or context or environment. For example, a camera incorporated on the medical device can estimate the mood of the user, or the distance to his face, or estimate the field of vision and provide appropriate responses. In another example, if the accelerometer history indicates that the patient is confused (number of accelerations recorded by the accelerometer above a certain predefined threshold for example), and/or in hypoglycemia state (which may cause the vision to be troubled) the medical system can display some predefined specific data. This automatic mode can be enabled by a cooperation of sensors.

The triggering information unit 220 can thus be associated to two main modes of operation (but intermediate modes remain possible). According to a first "on demand" mode 230, user data can be received from the user interface or from an input device or from a haptic device 231 (or from a physical button 232). According to a second "automatic" mode 240, data can be retrieved or received from body sensors 241 and/or environment sensors and/or contextual sensors 242.

The data priority scheme 250 can be associated with facts (numerical values) or knowledge base of facts 251, and/or with rules 252.

Display 210, user input 220 and data model 250 can be intermingled or combined. Relationships between these three abstractions can be associated with concepts such as influence, feedback, ponderation, limitation, activation, deactivation, control or command. For example, the data priority scheme 250 can influence or drive or control the display logic 210. For example, if a hypoglycemia probability or event is determined, associated alerts or values can preempt or replace any other display data. The data priority scheme 250 for example also can limit or control the Triggering Information unit (not shown). For example, a top priority being previously allocated to the basal rate can lead to the display of basal related data in case of any information received from the triggering information units 220 (any input device thereof). In other words, some user interactivity options may be deactivated or modified according to a certain state of the data priority scheme. In some cases, whatever sensors used by the user, the response in terms of displayed data can be the same (panic situation). According to others situations, different display responses can be provided in correspondence to different input devices. Likewise, the display logic 210 can restrict the data priority scheme 250 and/or command or control the triggering information unit. For example, a displayed alert of a severe hypoglycemia event may require a user confirmation before any other type of data can be further displayed.

A particular exploitation of time and date can be retrieved from the clock 202 and the calendar 203 can advantageously be made. If time indicates a night hour (range of about 1 am to about 5 am for example, and/or as confirmed by the accelerometer and/or confirmed by a sensor adapted to assess lighting conditions, i.e. darkness), then the data presenting the highest priority in terms of display priority can be the current basal rate (or the blood glucose level if the patient has continuous blood glucose monitoring). Calendar events also can be leveraged. For example, if the current date corresponds to the birthday of the user, then the likelihood of happiness may be increased. In particular, the likelihood that the user will have an important meal can be increased. So can associated boluses doses. Alternatively, if an anniversary of a sad family event is determined, then the state of the patient can imply a certain number of consequences regarding the user interactivity to be conducted (fewer reminders, less maintenance tasks if possible, etc.).

User interactivity and machine behavior can be defined by user-defined preferences or by machine learning or driven by rules retrieved from the network. The assessed state of the user or patient can indeed drive the interactivity model. The user profile 203 can comprise data such as the age of the patient, user preferences (in terms of display, reminders, alerts, type and frequency of desired interaction), habits (typical agenda and schedules, date of anniversaries of family members), health statistics, personal rules, as well as sources of data in which to retrieve—in real-time or not—additional personal data (such as email or social network website account for example). For example, just taking into account the age of the patient can lead to an effective user interaction. For a person over 60 years old, the system may introduce a bias in the pump preferences to increase the probability of switching to the zoom mode when certain criteria are met (automatic triggering information). These settings can be made manually (the user editing his permanent preferences) or can be set up automatically. The display preferences also can comprise particular rules. For example, when the presence of certain persons are detected in the vicinity of the patient wearing the medical device, a particular display mode can be deactivated (for example a zoom mode) or switched off when handled by the doctor or no longer by the child. User preferences also can be edited. For example, the user can edit his own list of priority ranks (see FIG. 8), that is each information type being associated with a priority rank (bolus dose is associated with rank 1, previous bolus the day before is associated with rank 2, date and time is associated with rank 3 for example).

Figure 3:
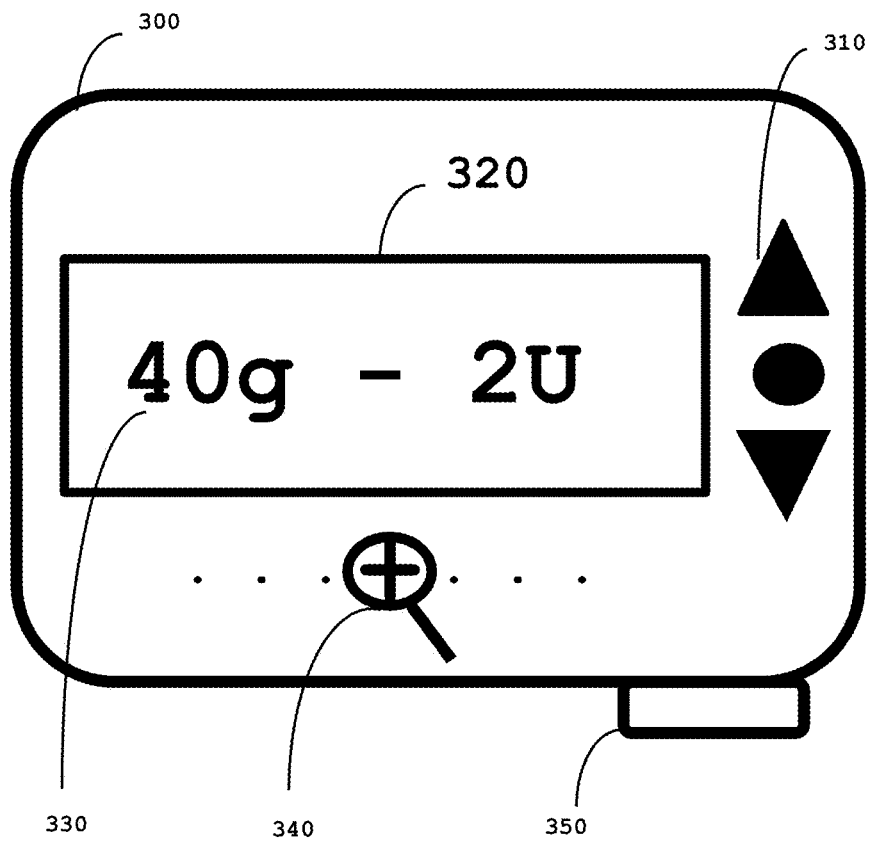
FIG. 3 illustrates electronic device such as an insulin pump provided with a display screen and a touch sensitive surface for triggering a zoom function according to an embodiment of the present disclosure.

FIG. 3 shows an electronic device such as an insulin pump provided with a display screen and a touch sensitive surface for triggering a zoom function. FIG. 3 shows an exemplary embodiment, namely an insulin pump provided with a screen. FIG. 3 comprises a pump housing 300, a user interface 310 comprising command and navigation buttons, a screen 320, data 330 being displayed on the screen, a zoom cursor 340, and a physical button 350. According to this embodiment, the triggering information can correspond to an action of the user on the zoom cursor 340. The cursor can be made of touch sensitive surface which can be separated from the screen 320 (according to other embodiments this input area can be part of a touch screen). The zoom cursor can enable the user to minimize or maximize the display of reviews selected from display data. The optional physical button 350 can have the same role or function as the zoom cursor. It also can modulate or modify the effects caused by the zoom cursor (for example, multiplication or smoothening of the effect generated by the zoom cursor, transformation of the text into speech or audio signal, etc.)

FIG. 3 discloses a medical infusion pump including a feature hereinafter called a "zoom badge." This feature can allow changing, or switching, back and forth between different pump displays (corresponding to different sizes of character fonts or symbols). Persons with diabetes presenting a constantly raised blood sugar level can lead to retina damages (blood vessels of the retina of the eye are damaged). Older persons can also have vision troubles. In order to adapt to these patients, data readability may need to be enhanced. According to FIG. 3, the size and type of the figures displayed can be increased upon the user selection and/or triggering of the "zoom badge." Alternatively, a negative view of the screen can be provided (the background color can be set to black and letters be set in white or vice-versa). Another possibility can be to use specific color codes (for example basal rate would be in red, current glucose value would be in orange, other information would be displayed in gray scales). Yet another possibility can be to only display uniform colored rectangles, corresponding to ranges of values. For example, a blood glucose value between about 80 and about 120 can correspond to a green rectangle, while a range between about 60 and about 80 can result in a light pink color rectangle and a range between about 120 and about 250 can appear in dark red (above about 250 a black rectangle can appear).

Such color code display can be adapted to children. An image comprising a vertical scale and a cursor also can be used for this audience. Extra-large screens can be provided with pumps that allow such features. Video capabilities also offer such similar developments (images of moods, animated characters, virtual animal reflecting the current state, etc.). In one embodiment, a separate triggering surface can be preferred. The surface can be touch-sensitive and can comprise several thresholds corresponding to several discrete zoom states (but the magnification or minimization of course can occur continuously). The triggering surface can be placed below the main display, for a better ergonomics and a faster activation. The zoom badge can use the well-known symbol "+" and the unambiguous symbol in the form of a magnifying glass. Users can use this triggering surface in bad lighting conditions (very bright sunlight or artificial light, during the night, etc.), during hypoglycemia or hyperglycemia events, when they have forgotten their glasses, when they are tired, when they want to show the display to other persons, etc. In order to change the mode of display rapidly and in an uncomplicated way (from normal to increased size back and forth for example), the user can simply press, or displace, the triggering surface and choose the appropriate zoom scale. Of course repeated action or sequences of actions can trigger other interface behaviors (such as combined sub selection of data and zoom functionality). According to an embodiment, the "zoom badge" can automatically be activated when touching the surface, the size of letters and figure can be moved up (or down). In addition, as long as the function is active, the symbol of the magnifying glass symbol can be lit in order to show that the zoom function is active. The lightening of the symbol can be obtained by a diode or an OLED screen for example. The zoom function can remain as long as the user touches the triggering screen. When the user ceases to touch the triggering surface, the display can return to its initial (normal) state.

A special attention can be allocated to this zoom function and associated user interface: the active switching can be combined with the determination or selection of the most important medically information to be displayed.

In a one embodiment, all non-important information can be ignored in the zoom process, i.e. only important information is magnified. For example, date and time do not appear during the magnification process, which only displays the blood glucose value. The determination of "important" versus "non-important" can be obtained by application of a certain threshold in a data model, possibly context-dependent or the distinction can be predefined.

In another embodiment, all previously displayed information can continue to be displayed but the geometrical proportions can be rearranged (size and shape of the data being displayed will vary according to each associated priority level). For example, the date and time can still be displayed but much smaller while the saved space can be used to increase the display size of the blood glucose value. A list by decreasing priority can be proposed: amounts of injected insulin, critical security indications (such as error or maintenance messages), steps for a particular function (in a message like "disconnect the pump and replace reservoir", the word "disconnect" can be magnified and others text strings can be diminished in size or completely hidden if the user presses again the zoom button). In other words, sub priorities can be defined to reach multiple levels of communication. In addition to the user friendliness of the interface, the security aspect can be essential. Therefore, an enhanced communication with the patient can lead to a better security. Misunderstandings or misreadings can be avoided by the disclosed methods and systems.

Figure 4:
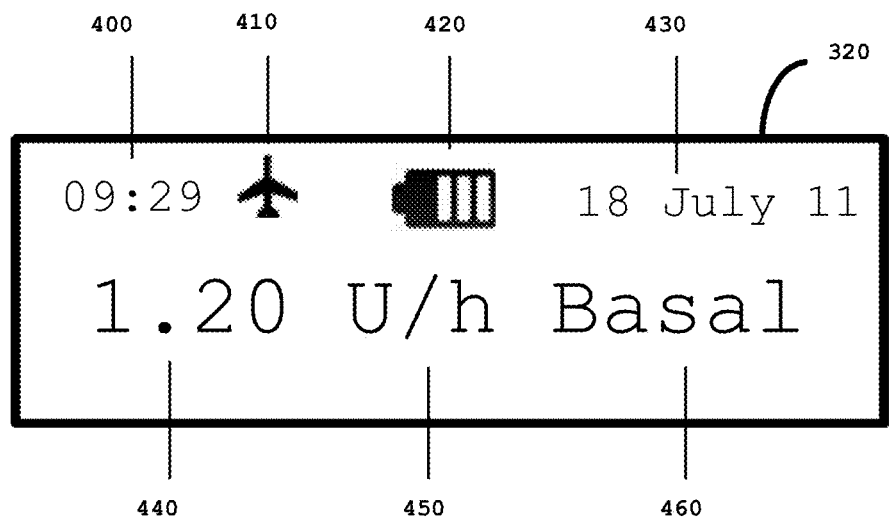
FIG. 4 illustrates example of the data displayed on a display screen which is part of an insulin pump or of a networked medical device part of a medical system for example according to an embodiment of the present disclosure.

FIG. 4 shows an example of the data displayed on a display screen which is part of an insulin pump. FIG. 4 shows an example of displayed data. The displayed data can comprise time information 400, (temporary) flight mode information 410 (no active communication channels), battery information 420, date or calendar information 320, numerical value 440, unit value 450, and type of information 460. FIG. 4, of course, is just one screenshot example, illustrating some of the types of data that can be displayed on an insulin pump.

In one embodiment, methods can handle the selection of a subset of data from a displayed dataset, i.e. from data which are already displayed. This can correspond to the real-life scenario, wherein a user can benefit from an enlargement of actual displayed data. In another embodiment, a method can handle the selection of a subset of data from a dataset, which dataset can include displayed and non-displayed data (broader scope). For example, if the blood glucose is low according to a certain threshold, then the speed of the decrease in values can also be of interest and may be also displayed. In this view, methods can provide even more than a contextual zoom functionality (triggered automatically and/or partly on-demand and based on the intelligent selection of existing parts of the display). The methods can enable and provide a further level of logic by adapting the display of data a step further (i.e. by including or taking into account a certain anticipation resulting from the assessment of a global situation—and not only from a limited point of view).

Figure 5:
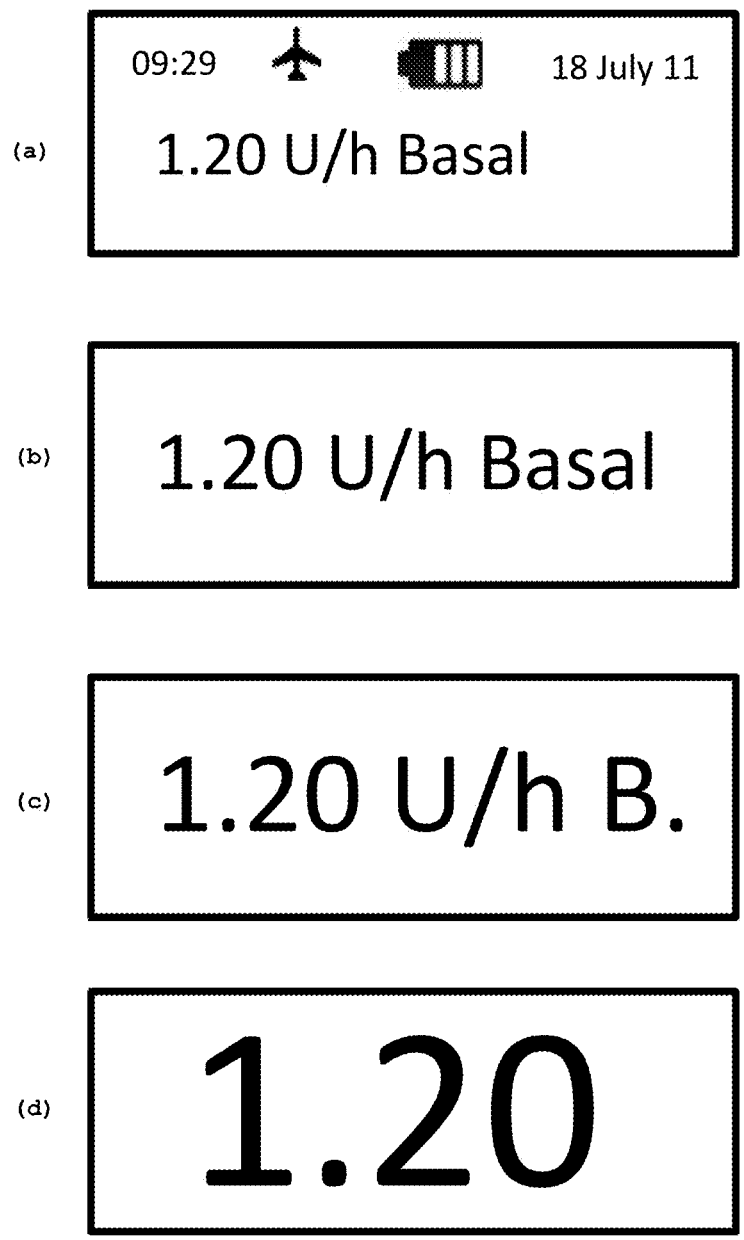
FIG. 5 illustrates examples of possible selections of the subset of data and the further modifications brought to the original displayed dataset according to an embodiment of the present disclosure.

FIG. 5 shows examples of possible selections of the subset of data and the further modifications brought to the original displayed dataset. FIG. 5 shows different illustrative screenshots, corresponding to different embodiments. The display (a) corresponds to the initial display. Upon the reception of triggering information, the initial display can be replaced by the screen illustrated in situation (b). In this view, information related to that date and time, flight mode and battery information have been skipped or wiped out or erased or hidden or masked. Simultaneously, the information related to the basal rate has been enlarged, i.e. is displayed in a larger format. Alternatively, the display (c) illustrates a further modification: the text has been shortened by the use of an acronym. In the display (d), the only information left is the basal rate. The patient may know what is implicit. In other words, the patient does not need to be distracted by other information than the very important figures. It is believed that diabetic patients even know how to discriminate between a basal rate and a bolus dose without any further indication (these values having very different ranges). A better efficiency can then be reached when the variable data is immediately and directly displayed. In this perspective further details can be displayed upon reception of triggering information. In one embodiment, the screen (d) can first be presented to the user and other information as illustrated in (a), (b) and (c) may be displayed only when requested.

Figure 6:
FIG. 6 illustrates other modes of display for enhanced readability according to an embodiment of the present disclosure.
Figure 6:
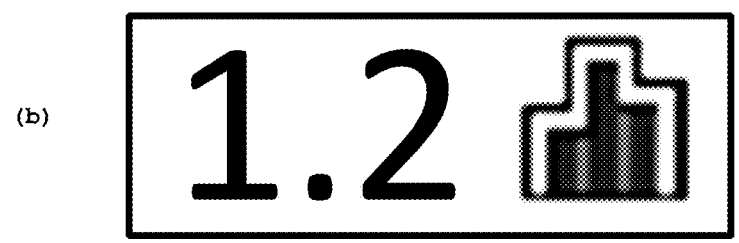
Figure 6:
Figure 6:
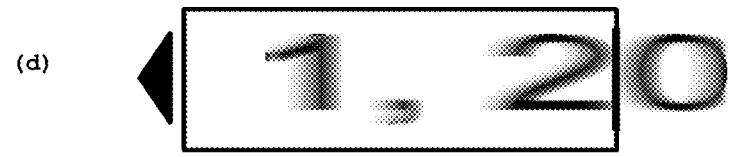

FIG. 6 shows other modes of display for enhanced readability. The display (a) can correspond to the initial display. The display (b) can present both iconic and textual communication. Many graphical forms can indeed be used: symbols, icons, images, videos, and/or textual forms. In other to optimize the space or format of the screen, different techniques can be used. The display (c) can correspond to the visual effect of a negative image. A positive image is a normal image. A negative image can be a total inversion of a positive image, in which light areas appear dark and vice versa. A negative color image is additionally color reversed, with red areas appearing cyan, greens appearing magenta and blues appearing yellow. This transformation may lead to enhanced readability. The display (d) can correspond to a video effect such as scrolling. In this mode, the surface of the screen may be optimized to the display.

Figure 7:
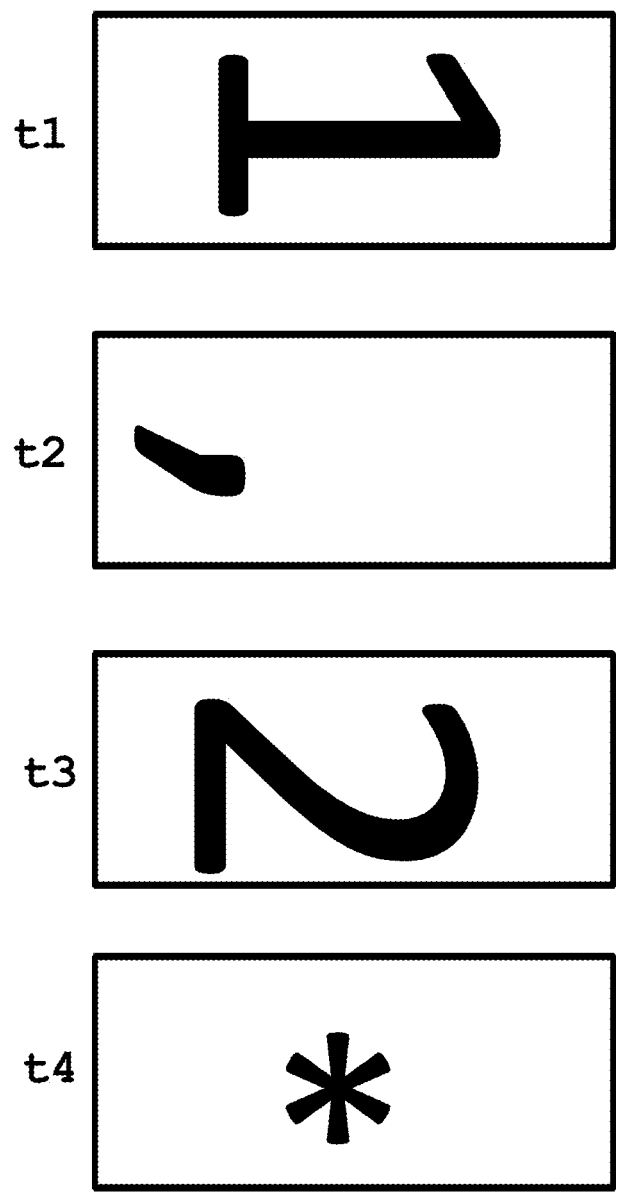
FIG. 7 illustrates an example of a full-screen optimization according to an embodiment of the present disclosure.

FIG. 7 shows an example of a full-screen optimization. FIG. 7 shows a sequence of screenshots, each screenshot corresponding to the maximum use of the available screen surface for the display of a number comprising several figures. At time t1, the first digit "1" is displayed using the entire screen. At time t2, the sign "," or "." is displayed using the entire screen. At time t3, the second digit "2" is displayed using the entire screen. At time t4, a graphical symbol "*" is displayed, meaning that the end or the beginning of the sequence has been reached. This example presents many variants: letters and digits can be rotated, different fonts can be used, time intervals may vary (the first digit may appear during 2 seconds while the second digit appears during a shorter time because being less important, for example).

As a summary regarding display modes, the display of information can be:
  temporary (the zoom occurs during a certain predefined number of seconds);
  intermittent (back and forth);
  permanent (see later); and/or
  "hybrid" (a number such as '123' in blood glucose level is displayed as a succession of '1' then '2' then '3' the letters covering the full available screen and a begin/stop information is provided (either the full '123' value either a symbol '*' or another convention).

FIG. 8 shows examples of a data priority scheme. As discussed, the scheme can comprise a knowledge base of facts, a set of rules, priority ranks, or other components. The priority scheme can be static (i.e. the components do not evolve over time) but it may also be dynamic (priority ranks evolve over time, and/or are responsive to local events and/or regulation rules and/or user profiles or preferences and/or contextual data and/or environmental data and/or ambient data).

Figures 8A, 8B:
FIG. 8 illustrates examples of a data priority scheme, which can be static or dynamic (not shown) according to an embodiment of the present disclosure.

Many patterns can be possible for the implementation of the data priority scheme. In FIG. 8a, each type of information (corresponding to different numerical values) can be associated with an absolute priority rank (or ranking). For example, information related to a bolus dose can be allocated to a level 1 while date and time information can be allocated with an inferior priority of 4. Optionally, an icon or a symbol can be associated with each type of information (for further use on display operations). Optionally again, each type of information can be associated with a different triggering option (user-defined or automatically driven by sensors). For example, the basal rate can be triggered by the user but cannot be triggered by one or more sensors. It is conceivable to limit the actions of sensors to the display of the glycemic state (blood glucose value) only. As indicated on the figure, numerous variants can exist. More subtle priority levels can be defined, conflicts can be anticipated, rules can be downloaded or retrieved in order to solve conflicts, etc.

FIG. 8b shows another embodiment, providing details and focus on the context of the display of data. Depending on the moments of the day (or the night), certain information may become more relevant. During the night, if a sensor detects a movement signaling that the patient is waking up, the basal rate and or the blood glucose level can be important information to display first. By contrast, cartridge state may not be as important. This assessment can be predefined, i.e. be defined according to statistics. But the assessment also can be dynamically defined. For example, if the cartridge is almost empty, the priority can be modified and the cartridge state may become the most important data to be displayed. User acknowledgement may be required in order to return to the predefined state. If sensors, together with the time information, detect that the user is likely to have lunch (movements are detected after a quiet period associated to a probability of the patient being working, thus indicating that the patient is moving to the cafeteria), the top priority data can be switched to the bolus menu. While being back at work, the main focus of the user can be information related to maintenance events. During the night, blood glucose value is likely to be considered as top priority information. In 2 seconds, with almost closed and tired eyes, one can be able to get the information directly (any other information, except the time maybe, may not be interesting for the user).

The disclosed methods and systems can establish or leverage a data priority scheme but can also anticipate for further menu selection and user actions. The display of data can be optimized as well as the entire user interaction model. While the disclosed methods and systems can enable a "proactive" user interaction, the latter may not become unpredictable (because a return to the normal state and behavior of the medical device can always remain possible). In reality, the medical device can try to be the most useful as possible but, when triggered, it can return into its "passive" state. An alternative comprises displaying, as a "second chance" mode, a second subset of data to the user (or according to an alternative manner). Successive user commands can enable such "switches" (for example one first press on a button can result in a first display mode, a second press can result in another mode, and at the third press the system can give up and return to its initial state). In this view, some opportunities are provided to the machine to show its "intelligence", but after a (limited) number of trials, the machine returns in passive or obeisance mode.

FIG. 9 shows examples of different embodiments and architectural choices, with different triggering information interfaces and/or different display devices and/or different communication modes. FIG. 9a shows an insulin pump with both a zoom cursor 910 and a physical triggering button 911. FIG. 9b shows an insulin pump provided with a zoom cursor 910 only. FIG. 9c shows an insulin pump provided with a physical triggering button 911 only. FIG. 9d shows an insulin pump without an embedded screen but provided with a projector 921. The projector can beam an image on a wall or on another surface 940. This projector can be a handheld projector (also known as a pocket projector or mobile projector or pico-projector). Handheld projectors involve miniaturized hardware and software that can project digital images onto any nearby viewing surface, such as a wall. Such a system can be compacted into one chip and can project a clear image, regardless of the physical characteristics of the viewing surface. The projector can be integrated with the insulin pump or embodied as a separate device communicating with the pump. FIG. 9d shows another embodiment, in which the pump 930 can comprise a method of drug injection and can be connected to the infusion set 938 by the tubing 931 and does not comprise an embedded display. In this case, the pump can communicate with the display 940 that is in the vicinity of the user or pump by a communication channel 933 (see a list of display devices 150 in FIG. 1).

Figure 10:
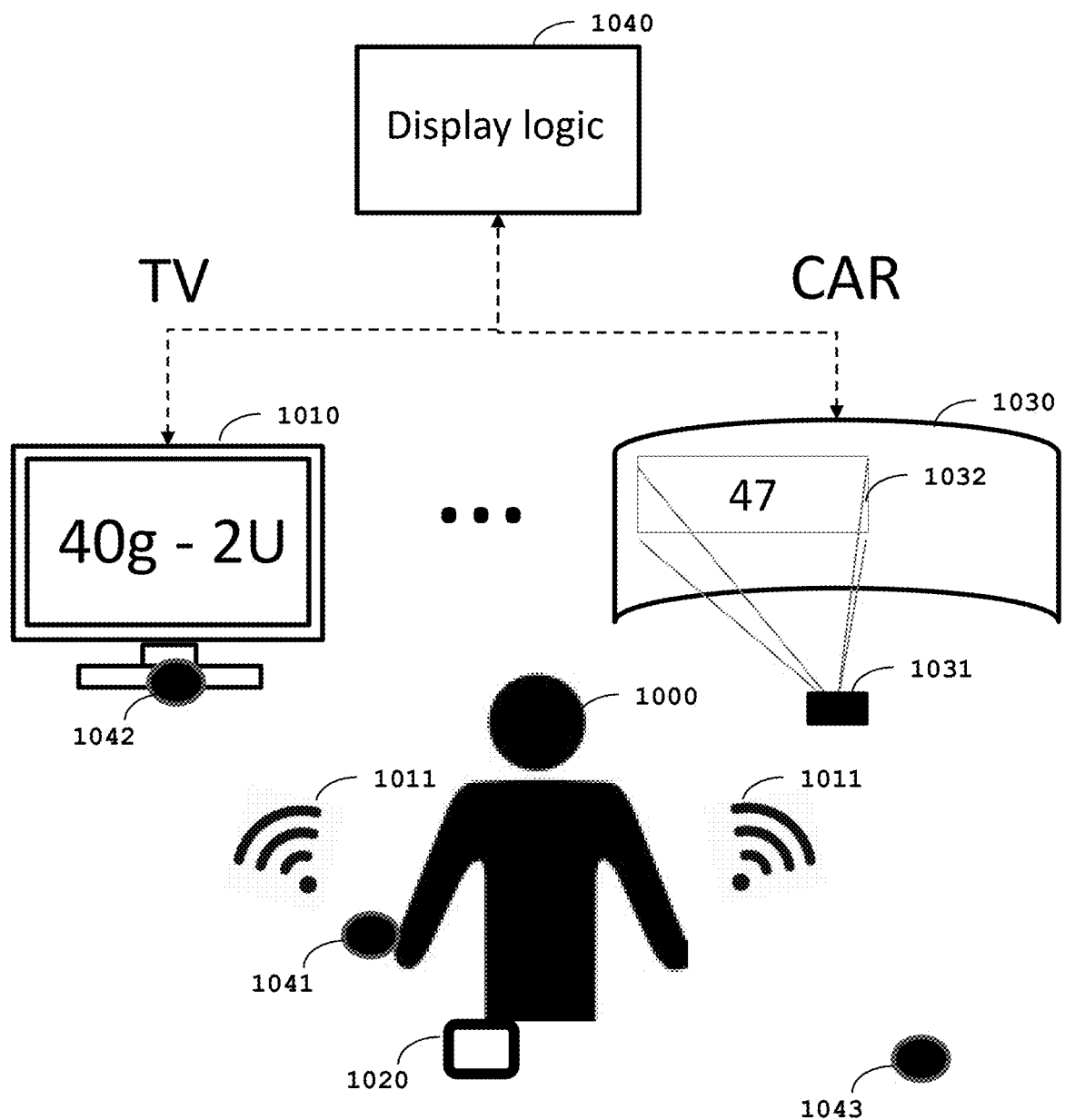
FIG. 10 illustrates other embodiments, with display devices such as a TV of car windscreen for example according to an embodiment of the present disclosure.

FIG. 10 shows an example of a real life situation. The user 1000 wears a medical device 1020 and a sensor measures his heart rate 1041. Those devices and sensors can communicate wirelessly with other devices. The environment sensor 1043 can be present in the environment and can provide geographical location data. In one example, the user is driving his car, in which the dashboard has a projector 1031 that communicates 1011 with the pump 1020 and/or the sensor 1041. The sensor 1041 can detect a high heart rate superior to the predefined threshold of 130 pm, while at the same time the continuous glucose monitoring device attached to the body of the user can determine a probability of an hypoglycemia event. By integrating the two values, the life situation assessment logic can determine that an alert should be raised. The display logic 210 or 1040 in turn can determine that a projector is present in the car and available for data display. The display logic 210 can trigger display of the value of the current measured value of blood glucose on the windscreen of the car (particular area for the display can be chosen, according to driving events, for example by avoiding acceleration moments and using possible stops of the car). The user being informed of his physiological state (of which he was not currently conscious of) can stop driving and can get a snack from a cafeteria nearby. The user can pass by a television present in the cafeteria. The sensor 1042 of the television 1010 in the cafeteria can communicate with the pump 1020 and, after authorization, authentication and privacy settings verification steps can prompt a meal recommendation (carbs and bolus dose taking into account the hypoglycemia) to the user.

Figure 11:
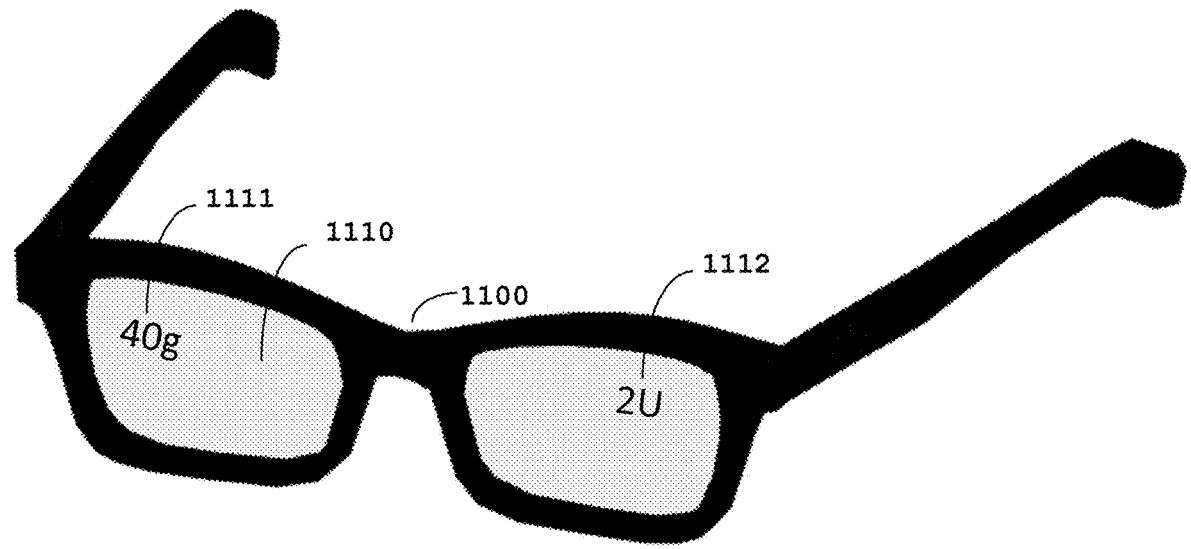
FIG. 11 illustrates example of a head-mounted display embodiment according to an embodiment of the present disclosure.

FIG. 11 shows an example of a head-mounted display embodiment. Since the user is likely to wear his pump or medical device with him all the time, but according to some scenarios, certain medical devices such as micro-pumps will not have screens. A display may be integrated in head-mounted displays. A head-mounted display can be a display device, worn on the head, which can have a small display optic in front of one (monocular) or each eye (binocular). A typical head-mounted display can have either one or two small displays with lenses and semi-transparent mirrors embedded in a helmet, eye-glasses (also known as data glasses) or visor. The display units are miniaturized and may include CRT, LCDs, or OLED. Head-mounted displays can differ in whether they can display just a computer generated image, show live images from the real world or a combination of both. Some head-mounted displays can allow a computer generated image to be superimposed on a real-world view. This is sometimes referred to as augmented reality or mixed reality. Combining real-world view with computer generated image can be done by projecting the computer generated image through a partially reflective mirror and viewing the real world directly. This method is often called "Optical See-Through". Combining real-world view with computer generated image can also be done electronically by accepting video from a camera and mixing it electronically with computer generated image. This method is often called "Video See-Through".

In such devices, the zoom functionality can present some specificity. The attention of the user may need to be properly managed to avoid unnecessary distractions. Appropriate areas in the field of vision may have to be determined. The balance and compromises to be made correspond to the mechanisms that allow for a balanced compromise, ponderation or selection of data to be displayed (with respect to substance), and the visual effect such as placement, surface, area, still or animated modes (with respect to the form).

Figure 12:
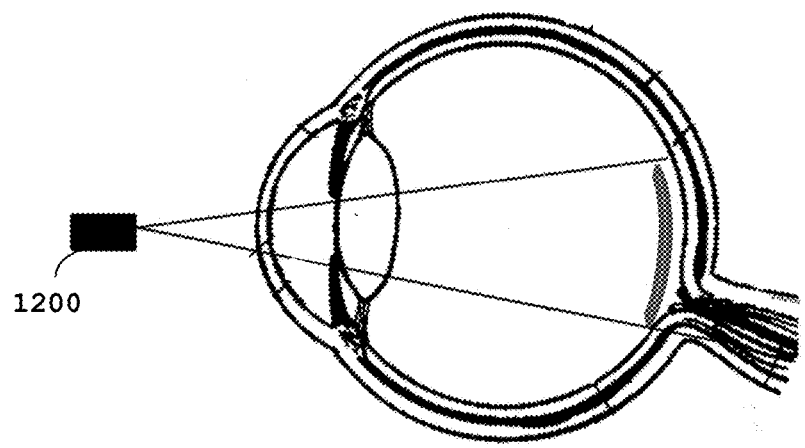
FIG. 12 illustrates example of a retinal display embodiment according to an embodiment of the present disclosure.

FIG. 12 shows an example of a retinal display embodiment. The user can wear a virtual retinal display 1200, also known as a retinal scan display or retinal projector. This display technology can draw a raster display (like a television) directly onto the retina of the eye. The use of a coherent source (such as a laser diode) allows the system to draw a diffraction limited spot on the retina. The light beam can be intensity modulated to match the intensity of the image being rendered. The user sees what appears to be a conventional display floating in space in front of them. Virtual retinal display system also can show an image in each eye with a very little angle difference for simulating three-dimensional scenes. Another important advantage can be privacy since only the intended user is able to see the image displayed.

The technical problem and solution can correspond to an optimization. Heterogeneous data can be provided by heterogeneous sensors that are integrated to provide an assessment of the mood or physiological state of the user and data are then being displayed in an appropriate manner with respect to the state. The appropriate manner of displaying can depend on the presence and accessibility of a heterogeneous display being in the vicinity of the user (support) and can depend on the data priority scheme allocated to the considered user (form and substance).

The present disclosure can encompass macro sensors (millimetric to centimetric scales), as well as micro sensors or even nano-sensors. The more miniaturized can result in more data. Nano sensors, for example, can let people monitor the level of a given drug in their blood in real-time (the monitoring can be continuous but it also can be real-time).

Associated effects or advantages stemming from the very presentation of information can be leveraged in (or by) certain specific contexts. The present disclosure can trigger and leverage such inherent (and non-technical) effects. The automatic visual display of the conditions prevailing or desirable in an apparatus or system can be a technical problem. Examples can define a technical system combining these non-technical display effects with technical input/triggering interfaces and (technical) data model, i.e. logic or decision based on data priority schemes and measures provided by sensors, technical methods enabling the displaying information. The data being handled can be medical data. These data can be regulated when it comes to advise the user or when the data can lead the patient or user to a therapeutic action, which is presently not the case (raw information, in the sense of measurements, are provided and not recommendations for action).

The present disclosure can take form of an entirely hardware embodiment, an entirely software embodiment or an embodiment containing both hardware and software elements. In one embodiment, the present disclosure is implemented in software, which includes but is not limited to firmware, resident software, microcode, etc. Furthermore, the present disclosure can take the form of a computer program product accessible from a computer-usable or computer-readable medium providing program code for use by or in connection with a computer or any instruction execution system. For the purposes of this description, a computer-usable or computer-readable can be any apparatus that can contain, store, communicate, propagate, or transport the program for use by or in connection with the instruction execution system, apparatus, or device.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A portable electronic device, comprising:
   at least one of a glucose sensor and an insulin pump;
   a hardware display; and
   a user input mechanism;
   wherein the portable electronic device is configured to:
   (a) receive triggering information, wherein the triggering information is one or more of input received from a user via the user input mechanism and information automatically provided by a second sensor, and the second sensor is selected from a group, or is a combination thereof, comprising: a sensor adapted to perform human face detection, a sensor adapted to evaluate the distance to a human eye, a sensor adapted to detect or analyze breath or smell, an accelerometer, a pedometer, an ambient lighting sensor, a sensor adapted to determine an ambient audio level, a sensor adapted to determine a geographic location, an electroencephalography EEG sensor, an electrocardiography ECG sensor, an electromyography EMG sensor, or a sensor adapted to determine a body temperature; and
   (b) display a selected subset of data using a normal display wherein the selected subset of data represents a single information type and wherein the device is further configured to display the selected subset of data using a modified display in response to receiving the triggering information, wherein the selection of the single information type represented by the selected subset of data is based on a data priority scheme that establishes a priority rank to at least two information types selected from the group of bolus dose, basal rate, occlusion, basal temporary rate, quick bolus, date and time, and wherein the modified display for displaying the selected subset of data is modified relative to the normal display for displaying the selected subset of data by removing one or more alphanumeric characters or symbols from the normal display of the selected subset of data, or, magnifying one or more alphanumeric characters or symbols in the normal display of the selected subset of data, and wherein the modified display of the selected subset of data differs from the normal display of the selected subset of data by at least one of:
   (i) using a scrolling video effect wherein the size of the selected subset of data is enlarged such that not all of the selected subset of data is displayable on the screen at once, and
   (ii) sequentially displaying single digits or symbols in a full screen view such that each single digit or symbol maximally occupies available screen surface on the hardware display.

2. The portable electronic device of claim 1, wherein when the received triggering information is the user input received via the user input mechanism, the portable electronic device is configured to display a first type of information of the plurality of information types.

3. The portable electronic device of claim 1, wherein when the received triggering information is from the second sensor, the portable electronic device is configured to display a second type of information of the plurality of information types.

4. The portable electronic device of claim 1, wherein the user input mechanism is selected from a group, or is a combination thereof, comprising: a touch sensitive surface, a physical button, a portion of a capacitive or of a resistive touchscreen, a motion sensing input sensor adapted to interpret gestures, a sensor responsive to a voice or an audio signal, or an eye-tracking sensor adapted to interpret human eye movements.

5. The portable electronic device of claim 1, wherein the portable electronic device comprises the insulin pump and the glucose sensor.

6. The portable electronic device of claim 1, wherein the data priority scheme is predefined.

7. The portable electronic device of claim 1, wherein the hardware display comprises one or more of: a projector, a television, a computer, a telephone, a headed-mounted display device.

8. The portable electronic device of claim 1, wherein the information from the glucose sensor and/or from the insulin pump is associated with diabetes data including one or more of blood glucose data, bolus dose, bolus type, basal rate, temporary basal rate, calibration reminder, occlusion probability or event, leakage probability or event, hypoglycemia probability or event, hyperglycemia probability or event, ketosis or ketoacidosis probability or event, or maintenance event or reminder.

9. The portable electronic device of claim 1, further comprising a multi-injection device.

10. The portable electronic device of claim 1, wherein the displaying of a selected subset of data includes abbreviating a displayed unit of measure of a physiological value pertaining to the user.

11. The portable electronic device of claim 1, wherein when the received triggering information is from the second sensor, the portable electronic device is configured to display information related to the insulin pump.

12. The portable electronic device of claim 1, wherein the portable electronic device is configured to change the priority rank of at least one of the information types as a function of at least one of: time of day, work status and meal intake.

13. A portable electronic device, comprising:
- an insulin pump;
- a hardware display; and
- a user input mechanism;
- wherein the portable electronic device is configured to:
  - (a) receive triggering information automatically provided by a sensor selected from a group, or a combination thereof, comprising: a sensor adapted to perform human face detection, a sensor adapted to evaluate the distance to a human eye, a sensor adapted to detect or analyze breath or smell, an accelerometer, a pedometer, an ambient lighting sensor, a sensor adapted to determine an ambient audio level, a sensor adapted to determine a geographic location, an electroencephalography EEG sensor, an electrocardiography ECG sensor, an electromyography EMG sensor, or a sensor adapted to determine a body temperature; and
  - (b) display a selected subset of data using a normal display wherein the selected subset of data represents a single information type and wherein the device is further configured to display the selected subset of data using a modified display in response to receiving the triggering information, wherein the selection of the single information type represented by the selected subset of data is based on a data priority scheme that establishes a priority rank to a plurality of information types, the information types relating to the insulin pump, and wherein the modified display for displaying the selected subset of data is modified relative to the normal display for displaying the selected subset of data by removing one or more alphanumeric characters or symbols from the normal display of the selected subset of data, or, magnifying one or more alphanumeric characters or symbols in the normal display of the selected subset of data, and wherein the modified display of the selected subset of data differs from the normal display of the selected subset of data by at least one of:
    - (i) using a scrolling video effect wherein the size of the selected subset of data is enlarged such that not all of the selected subset of data is displayable on the screen at once, and
    - (ii) sequentially displaying single digits or symbols in a full screen view such that each single digit or symbol maximally occupies available screen surface on the hardware display.

14. The portable electronic device of claim 13, wherein the information related to the insulin pump is one or more of basal rate, date and time and bolus dose.

15. The portable electronic device of claim 13, wherein the portable electronic device is configured to change the priority rank of at least one of the information types as a function of at least one of: time of day, work status and meal intake.

\* \* \* \* \*